(12) United States Patent
Diao et al.

(10) Patent No.: US 10,670,815 B2
(45) Date of Patent: Jun. 2, 2020

(54) OPTICAL FIBER COUPLING RELIABILITY

(71) Applicant: Novartis AG, Basel (CH)

(72) Inventors: Chenguang Diao, Irvine, CA (US); Alireza Mirsepassi, Irvine, CA (US); Michael J. Papac, North Tustin, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 15/995,568

(22) Filed: Jun. 1, 2018

(65) Prior Publication Data

US 2018/0284360 A1 Oct. 4, 2018

Related U.S. Application Data

(63) Continuation of application No. 15/647,476, filed on Jul. 12, 2017, now Pat. No. 10,012,800.

(60) Provisional application No. 62/361,612, filed on Jul. 13, 2016.

(51) Int. Cl.
*G02B 6/38* (2006.01)
*G02B 1/11* (2015.01)
*G02B 6/02* (2006.01)
*A61F 9/007* (2006.01)
*A61F 9/008* (2006.01)

(52) U.S. Cl.
CPC ............ *G02B 6/3861* (2013.01); *A61F 9/007* (2013.01); *G02B 1/11* (2013.01); *G02B 6/02395* (2013.01); *G02B 6/3801* (2013.01); *G02B 6/382* (2013.01); *G02B 6/3813* (2013.01); *A61F 9/008* (2013.01)

(58) Field of Classification Search
CPC .... G02B 6/255; G02B 6/2551; G02B 6/3801; G02B 6/3861
See application file for complete search history.

(56) References Cited

U.S. PATENT DOCUMENTS

| | | | | |
|---|---|---|---|---|
| 6,168,319 B1* | 1/2001 | Francis | ............... | G02B 6/2937 385/55 |
| 7,440,652 B2* | 10/2008 | Wang | ................... | G02B 6/2937 385/33 |
| 7,513,696 B2* | 4/2009 | Wada | ................... | G02B 6/3874 385/88 |
| 8,279,542 B2* | 10/2012 | Tanaka | ................... | G02B 6/327 359/819 |
| 2003/0091294 A1* | 5/2003 | Sasaki | ................... | G02B 6/3809 385/71 |
| 2004/0175073 A1* | 9/2004 | Grinderslev | ............. | G02B 6/32 385/34 |

* cited by examiner

*Primary Examiner* — Omar R Rojas

(57) ABSTRACT

Improved optical fiber coupling reliability is realized by improving structures and materials used at the fiber joint. When ceramic ferrules are used at the fiber joint, the penetration of a UV-cured optical adhesive between the ceramic ferrules and the fiber ends is avoided or prevented, while an anti-reflective coating, an uncured optical adhesive, or a refractive index matching gel may be applied between the ceramic ferrules. When glass ferrules are used at the fiber joint, the UV-cured optical adhesive may be applied and fully cured between the glass ferrules and the fiber ends.

8 Claims, 4 Drawing Sheets

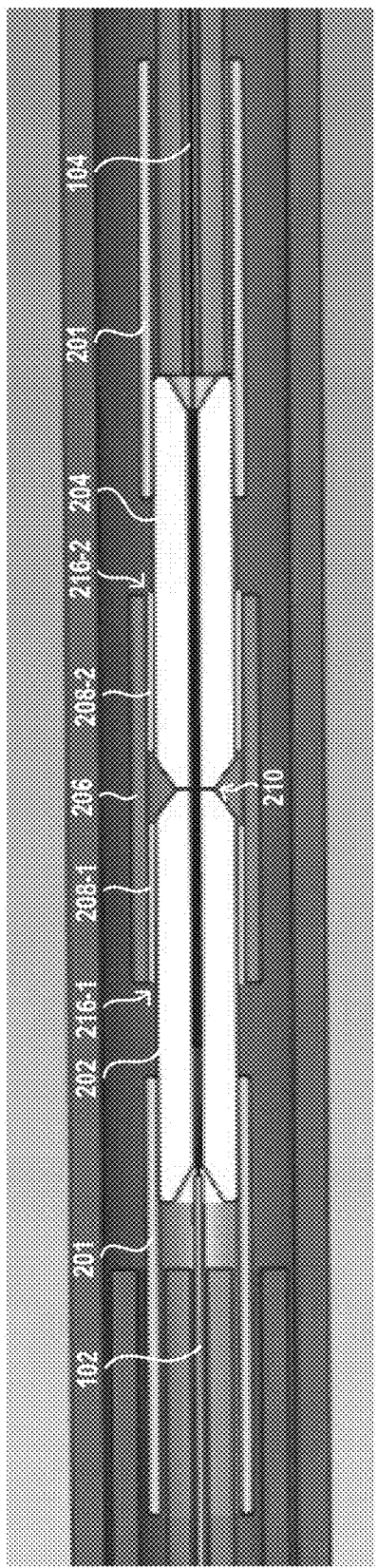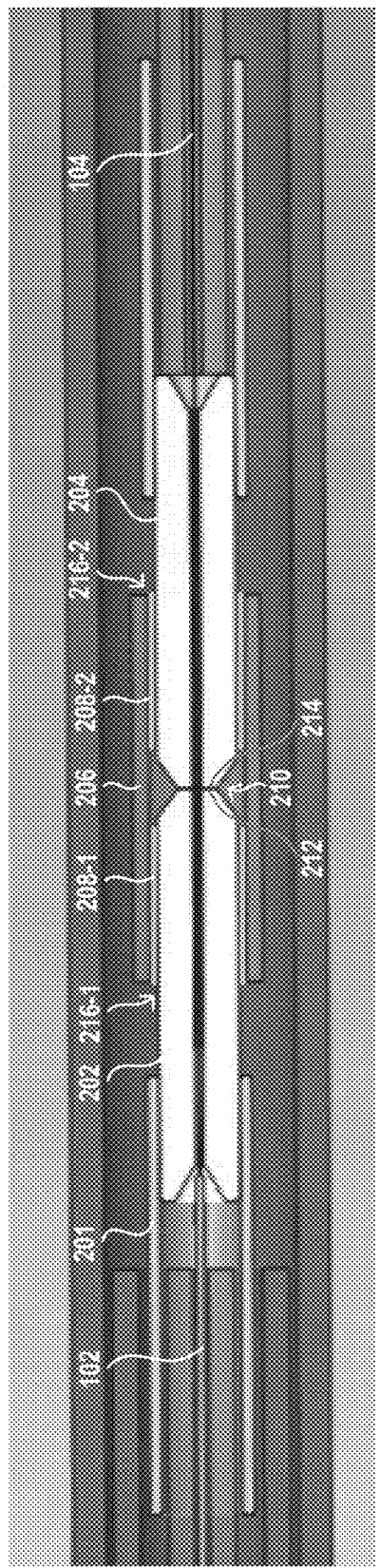
FIG. 2A
FIG. 2B

OPTICAL FIBER COUPLING RELIABILITY

BACKGROUND

Field of the Disclosure

The present disclosure relates to optical fibers, and more specifically, to improved optical fiber coupling reliability.

Description of the Related Art

In ophthalmology, eye surgery, or ophthalmic surgery, is performed on the eye and accessory visual structures. For example, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others. Other types of ophthalmic surgeries include operations on the eye lens, such as cataract surgery, and the cornea.

During ophthalmic surgery, an ophthalmologist typically uses a surgical microscope to view the eye, while surgical instruments may be introduced to perform any of a variety of different procedures. The surgical microscope provides imaging and optionally illumination of the eye during ophthalmic surgery. Additionally, external illumination during ophthalmic surgery, such as in the posterior region during vitreoretinal surgical procedures, may be provided using an optical fiber to provide suitable illumination. The optical fiber used in during ophthalmic surgery may have a small diameter to have minimum insertion trauma on the eyes, and in certain cases the small diameter fibers with the same or dissimilar materials are coupled to achieve illumination in the eye. In particular, the coupling of very small dissimilar fiber materials for relatively high optical power may be difficult or impossible to achieve using conventional fiber splicing methods.

SUMMARY

In one aspect, a disclosed optical fiber includes a proximal fiber coupled to a distal fiber at a fiber joint. In the optical fiber, the fiber joint may further include a first ferrule connectorizing the proximal fiber, a second ferrule connectorizing the distal fiber and opposing the first ferrule, and a glass sleeve surrounding the first ferrule and the second ferrule to enable optical coupling between the proximal fiber and the distal fiber. In the optical fiber, the glass sleeve may be bonded at one end of the glass sleeve using an ultraviolet (UV)-cured optical adhesive to a first outer surface of the first ferrule and the glass sleeve may be bonded at another end of the glass sleeve using the UV-cured optical adhesive to a second outer surface of the second ferrule, while fiber joint may sustain a luminous flux of at least 70 lumens transmitted through the proximal fiber to the distal fiber without degradation for at least 30 minutes.

In any of the disclosed embodiments of the optical fiber assembly, the first ferrule and the second ferrule may be both ceramic ferrules, while the UV-cured optical adhesive may not be present in the fiber joint between the first ferrule and the second ferrule.

In any of the disclosed embodiments of the optical fiber assembly, the fiber joint may further include an anti-reflective coating applied to the first ferrule at the proximal fiber and applied to the second ferrule at the distal fiber. In the optical fiber, the anti-reflective coating may reduce reflection of light between the proximal fiber and the distal fiber.

In any of the disclosed embodiments of the optical fiber assembly, the fiber joint may further include an uncured optical adhesive applied between the first ferrule and the second ferrule. In the optical fiber, the uncured optical adhesive may remain in the liquid phase in the fiber joint.

In any of the disclosed embodiments of the optical fiber assembly, the distal fiber may be used for illumination of a human eye during ophthalmic surgery.

In any of the disclosed embodiments of the optical fiber assembly, the fiber joint may include a refractive index matching gel between the first ferrule and the second ferrule.

In any of the disclosed embodiments of the optical fiber assembly, the proximal fiber and the distal fiber may be made of dissimilar materials.

In any of the disclosed embodiments of the optical fiber assembly, at least one of the proximal fiber and the distal fiber may have a diameter less than 50 micrometers.

In any of the disclosed embodiments of the optical fiber assembly, the first ferrule and the second ferrule may both be glass ferrules, while the UV-cured optical adhesive may also be present between the first ferrule and the second ferrule.

In any of the disclosed embodiments of the optical fiber, the fiber joint may transmit incoherent light from at least one of a Xenon lamp source and a light-emitting diode (LED) source.

In any of the disclosed embodiments of the optical fiber, the fiber joint may transmit coherent light from a white laser source.

In another aspect, a method for coupling optical fibers is disclosed. The method may include connectorizing a proximal fiber into a first ferrule and connectorizing a distal fiber into a second ferrule. The method may also include aligning the proximal fiber in the first ferrule and the distal fiber in the second ferrule in an alignment fixture, while a glass sleeve is placed around one of the proximal fiber or the distal fiber. The method may further include sliding the glass sleeve over a fiber joint between the first ferrule and the second ferrule, while the glass sleeve extends over the first ferrule and the second ferrule. The method may further include applying first UV-cured optical adhesive to a first end of the glass sleeve to bond the glass sleeve to the first ferrule, and applying second UV-cured optical adhesive to a second end of the glass sleeve to bond the glass sleeve to the second ferrule. Before the first UV-cured optical adhesive and the second UV-cured optical adhesive reach the fiber joint, the method may include curing the first UV-cured optical adhesive and the second UV-cured optical adhesive with UV light through the glass sleeve. In the method, the fiber joint may sustain a luminous flux of at least 70 lumens transmitted through the proximal fiber to the distal fiber without degradation for at least 30 minutes.

In any of the disclosed embodiments of the method, the first ferrule and the second ferrule may both be ceramic ferrules, while the UV-cured optical adhesive may not be present in the fiber joint between the proximal fiber and the distal fiber.

In any of the disclosed embodiments of the method, prior to the aligning, the method may further include applying an anti-reflective coating to the first ferrule at the proximal fiber and to the second ferrule at the distal fiber. In the method, the anti-reflective coating may reduce reflection of light between the proximal fiber and the distal fiber.

In any of the disclosed embodiments of the method, prior to sliding the glass sleeve over the fiber joint, the method may further include applying an uncured optical adhesive between the first ferrule and the second ferrule. In the method, the uncured optical adhesive may remain in the liquid phase in the fiber joint.

In any of the disclosed embodiments of the method, prior to sliding the glass sleeve over the fiber joint, the method may include applying a refractive index matching gel between the first ferrule and the second ferrule.

In any of the disclosed embodiments of the method, the distal fiber may be used for illumination of a human eye during ophthalmic surgery.

In any of the disclosed embodiments of the method, the proximal fiber and the distal fiber may be made of dissimilar materials.

In any of the disclosed embodiments of the method, at least one of the proximal fiber and the distal fiber may have a diameter less than 50 micrometers.

In any of the disclosed embodiments of the method, the first ferrule and the second ferrule may both be glass ferrules, while the method may further include, prior to sliding the glass sleeve over the fiber joint, applying third UV-cured optical adhesive in the fiber joint between the first ferrule and the second ferrule.

In any of the disclosed embodiments of the method, the fiber joint may transmit incoherent light from at least one of a Xenon lamp source and a light-emitting diode (LED) source.

In any of the disclosed embodiments of the method, the fiber joint may transmit coherent light from a white laser source.

BRIEF DESCRIPTION OF THE DRAWINGS

For a more complete understanding of the present invention and its features and advantages, reference is now made to the following description, taken in conjunction with the accompanying drawings, in which:

FIGS. 2A and 2B are diagrams of selected embodiments of an optical fiber joint having improved reliability;

DESCRIPTION OF PARTICULAR EMBODIMENT(S)

Figure 1:
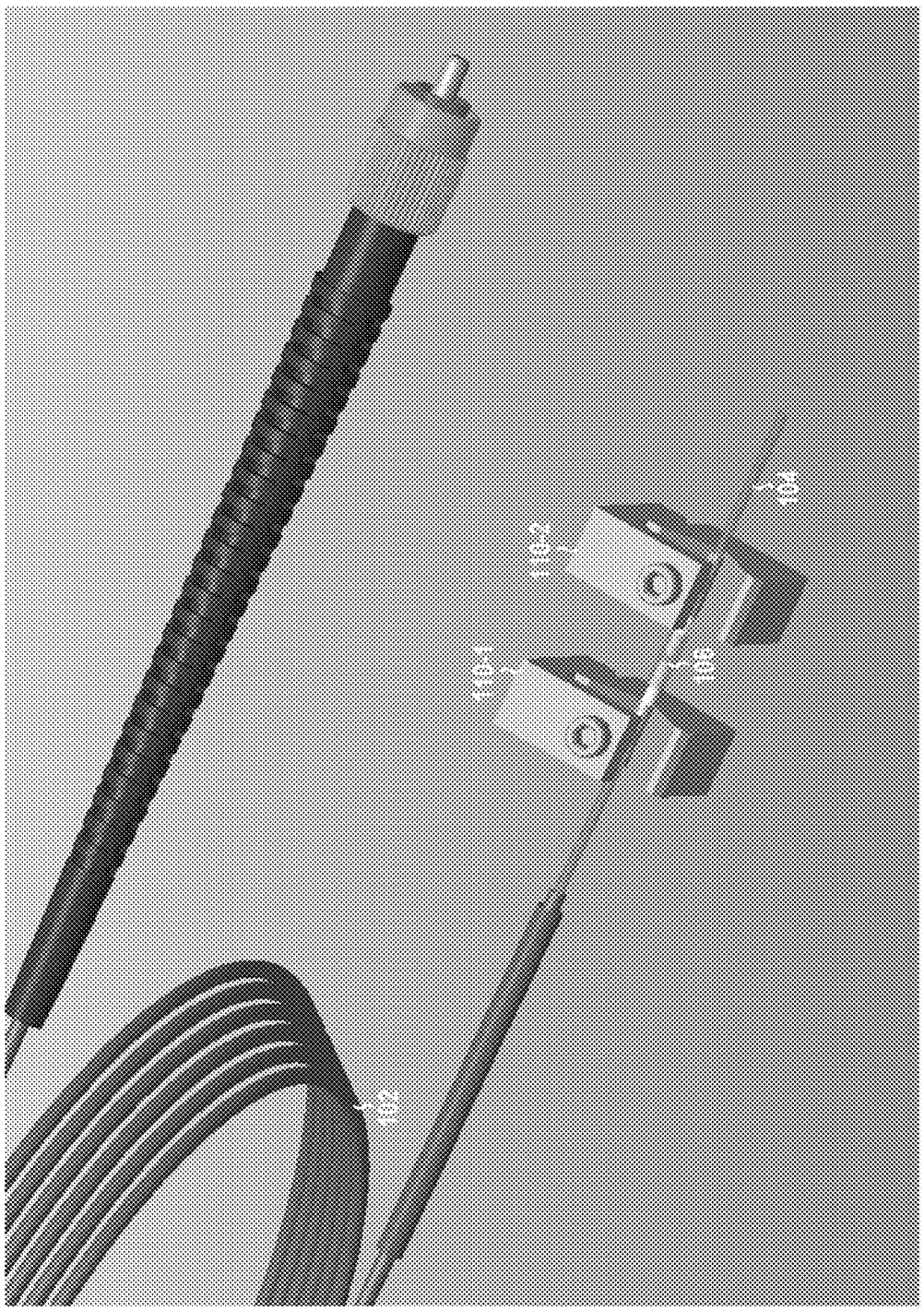
FIG. 1 is a depiction of an embodiment of an optical fiber assembly.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, in certain examples of ophthalmic surgery, such as in minimally-invasive eye surgeries, small diameter fibers with the same or dissimilar optical materials are coupled to form an optical fiber that provides illumination to the human eye. It has been observed that conventional fiber splicing techniques may not result in reliable fiber joints for the case of small diameter fibers (<50 µm diameter). Particularly for the case of very small fibers (<40 µm diameter) with dissimilar fiber materials, achieving a fiber splicing may be difficult, while an unsuitable degree of failure may be observed in conventional fiber joints, due to the very different thermal properties of the two different fiber materials (such as silica and borosilica, among other fiber materials). In addition, no passive alignment technique (without relying on actual light transmission during the coupling operation) is known for coupling very small fibers due to the difficulty of manufacturing small inner diameter ferrules and precision sleeves having tight tolerances and high inner-outer diameter concentricity. Thus, an accurate alignment and coupling is achieved by inserting the very small fibers into available ferrules, while actively aligning the fibers using the measured light transmitted and glue bonding them together.

However, conventional techniques for glue bonding fiber joints, particularly for very small diameter fibers where dissimilar fiber materials are coupled, may not yield a fiber joint that can withstand the high luminous flux used for surgical illumination, such as during ophthalmic surgery. As a result, such conventional fiber joints have been observed to prematurely fail in a very short time and are not considered sufficiently reliable for surgical or other medical applications.

Because a high luminous flux (up to 70 lumens) may be applied to a small diameter fiber for purposes of illumination during ophthalmic surgery, the irradiance in the fiber joint can be very high. As a result, many conventional fiber joints are subject to low reliability because the fiber joint may not be sufficiently robust to withstand the high irradiance, even for a relatively short service life of a single surgery, which may typically be less than 1 hour in duration, less than 30 minutes in duration, or less than 20 minutes in duration. One example of a failure mode of a conventional fiber joint results from an insufficient curing of an ultraviolent (UV)-cured optical adhesive that is used at the fiber joint and is applied between the two fiber ends being joined. The failure of such a conventional fiber joint may result from UV shadows due to the UV-opaque ceramic ferrules that are used. Therefore, when the fiber joint is exposed to the high power illumination, the non-cured UV-cured adhesive (which is disadvantageously located precisely where the two fibers meet in the fiber joint) remains unstable and may induce a tiny fiber misalignment within the fiber joint, which causes the light path to become partially blocked, resulting a 'hot spot' between the two fibers. The resulting thermal effects may, in turn, worsen the misalignment between the two fibers and eventually lead to failure of the fiber joint.

As will be described in further detail, the inventors of the present disclosure have developed methods for improved optical fiber coupling reliability. The methods for improved optical fiber coupling reliability disclosed herein may enable two small (or very small) diameter fibers to be coupled in a reliable manner with a high transmission efficiency. The methods for improved optical fiber coupling reliability disclosed herein may enable a slightly larger diameter fiber to be coupled with a very small diameter fiber using an improved fiber joint. The methods for improved optical fiber coupling reliability disclosed herein may enable reliable high optical power handling capability at the improved fiber joint. The methods for improved optical fiber coupling reliability disclosed herein may enable coupling of two optical fibers comprised of similar or dissimilar materials using the improved fiber joint. The methods for improved optical fiber coupling reliability disclosed herein may result in an improved fiber joint that is reliable and can efficiently deliver high power illumination for ophthalmic surgery without failure during the duration of the surgery.

Referring now to the drawings, FIG. 1, illustrates selected elements of an embodiment of an optical fiber assembly 100. It is noted that FIG. 1 is a schematic illustration and is not drawn to scale. In FIG. 1, optical fiber assembly 100 is comprised of a proximal fiber 102 and a distal fiber 104. The fibers 102, 104 are shown in FIG. 1 with cladding and sheathing, such that the actual optical fiber core is not visible. Specifically, proximal fiber 102 may have an optical connector at one end for coupling to an optical source (not shown), which may be an incoherent light source or a coherent light source. An example of an incoherent broadband light source is a Xenon lamp or a light-emitting diode (LED), while an example of a coherent light source may be a white light laser source. Proximal fiber 102 and distal fiber 104 are shown connectorized with respective ferrules at the end of the fibers. Connectorizing an optical fiber involves stripping the fiber down to the cladding surrounding the fiber core and inserting the fiber into the inner diameter of a ferrule. Then, the fiber is glued into the ferrule using an adhesive. After gluing, the end of the ferrule and the end of the fiber may be polished to yield a precise flat and smooth surface for joining to another connectorized fiber. The polishing operation may be performed with a plurality of connectorized fiber ends in aggregate.

Also shown in FIG. 1 is fiber joint 106, which is an optical coupling between one end of proximal fiber 102 and one end of distal fiber 104. As shown, fiber joint 106 is formed after proximal fiber 102 in a first ferrule is precisely aligned with distal fiber 104 in a second ferrule in an alignment fixture 110. As shown, proximal alignment fixture 110-1 and distal alignment fixture 110-2, in which proximal fiber 102 and distal fiber 104 are respectively mounted, may each be independently translated for alignment purposes, such as along three axes of movement in X, Y, Z directions for any arbitrary Cartesian space. As will be described in the following figures and description, fiber joint 106 may represent any of various embodiments of an improved fiber joint having improved optical fiber coupling reliability, as disclosed herein.

Referring now to FIG. 2A, selected elements of an embodiment of an optical fiber joint 106-1 (or simply 'fiber joint') are shown. FIG. 2A is a schematic diagram and is not drawn to scale. In FIG. 2A, fiber joint 106-1 is shown in a cross-sectional view, in which the depicted elements may be assumed to be radially symmetrical about a center line extending parallel to the optical fibers. In FIG. 2A, fiber joint 106-1 depicts an optical coupling between ends of proximal fiber 102 and distal fiber 104, which have been stripped down to their respective cladding surrounding the fiber core and connectorized, prior to being inserted into respective tubes 201 for supporting the elements involved in the coupling joint, as shown.

It is noted that proximal fiber 102 or distal fiber 104 may be less than 100 µm in diameter in various embodiments. In some embodiments, proximal fiber 102 or distal fiber 104 may be 50 µm or less in diameter. In some embodiments, proximal fiber 102 or distal fiber 104 may be 40 µm or less in diameter. In some embodiments, proximal fiber 102 or distal fiber 104 may be 30 µm or less in diameter. In some embodiments, proximal fiber 102 or distal fiber 104 may be 20 µm or less in diameter. It is also noted that fiber joint 106, including the various embodiments in the figures described below, may be suitable to transmit a luminous flux of at least 70 lumens for at least 60 minutes continuously without failure. In some embodiments, fiber joint 106 may transmit a luminous flux of at least 50 lumens for at least 60 minutes continuously without failure. In some embodiments, fiber joint 106 may transmit a luminous flux of at least 70 lumens for at least 30 minutes continuously without failure. In some embodiments, fiber joint 106 may transmit a luminous flux of at least 50 lumens for at least 30 minutes continuously without failure.

Specifically, in FIG. 2A, a first ferrule 202 connectorizes an end of proximal fiber 102, while a second ferrule 204 connectorizes an end of distal fiber 104 in an opposing manner, as described previously. First ferrule 202 and second ferrule 204 may be inserted into tubes 201, respectively, for supporting fiber joint 106-1 during forming and bonding, and to maintain alignment in an alignment fixture. Accordingly, the polished ends of proximal fiber 102 and distal fiber 104 meet at interface 210 where the ends of first ferrule 202 and second ferrule 204 meet within glass sleeve 206. As shown in fiber joint 106-1, first ferrule 202 and second ferrule 204 are both ceramic ferrules and are thus opaque to light, including UV light. Glass sleeve 206 is transparent to light, including UV light.

In a conventional fiber joint (not shown), the fibers in the two ferrules are aligned and then a UV cured optical adhesive is applied directly to the fiber joint before the glass sleeve is pulled over the fiber joint. Then the UV cured optical adhesive is cured using UV light, albeit with the limitations described above as a result of shadows from the ferrules, which may result in insufficient curing precisely where the two fibers meet.

As shown in FIG. 2A, fiber joint 106-1 is made with improved optical fiber coupling reliability. Prior to aligning first ferrule 202 and second ferrule 204 in an alignment fixture, such as alignment fixture 110 in FIG. 1, glass sleeve 206 may be inserted around one of proximal fiber 102 or distal fiber 104. Then first ferrule 202 and second ferrule 204 may be aligned such that a desired transmission of light is observed at distal fiber 104 (active optical alignment). After the alignment, glass sleeve 206 may be placed over an interface 210 between first ferrule 202 and second ferrule 204, as shown in FIG. 2A.

After glass sleeve 206 is positioned, a UV-cured optical adhesive 208 may be applied. UV-cured optical adhesive 208 may be any suitable UV-cured optical adhesive, such as an epoxy or other bonding agent. Specifically, at a first end 216-1 of glass sleeve 206, first UV-cured optical adhesive 208-1 may be introduced and may penetrate the gap between glass sleeve 206 and first ferrule 202 towards interface 210, as shown. Similarly, at a second end 216-2 of glass sleeve 206, second UV-cured optical adhesive 208-2 may be introduced and may penetrate the gap between glass sleeve 206 and first ferrule 202 towards interface 210, as shown. Because glass sleeve 206 is transparent, the penetration of UV-cured optical adhesive 208-1, 208-2 in opposing directions towards interface 210 may be observed. Before UV-cured optical adhesive 208-1, 208-2 reaches interface 210, UV light may be applied to cure UV-cured optical adhesive 208. As a result, UV-cured optical adhesive 208 bonds glass sleeve 206 to an outer cylindrical surface of both first ferrule 202 and second ferrule 204, thereby creating an optical coupling in fiber joint 106-1, without introducing any UV-cured optical adhesive 208 at interface 210 between first ferrule 202 and second ferrule 204, including between proximal fiber 102 and distal fiber 104. In this manner, improved optical fiber coupling reliability is realized in fiber joint 106-1.

FIG. 2B depicts selected elements of an embodiment of an optical fiber joint 106-2 that includes all the elements described above for fiber joint 106-1 in FIG. 2A. FIG. 2B is a schematic diagram and is not drawn to scale. However, in fiber joint 106-2, anti-reflective coatings 212 and 214 have additionally been applied to the end surfaces of the first ferrule 202 (including a first end surface of proximal fiber 102) and second ferrule 204 (including a second end surface of distal fiber 104) respectively. For example, anti-reflective coatings 212, 214 may be applied to the protruding end of first ferrule 202 and second ferrule 204, respectively, prior to the operations for forming optical fiber joint 106-2, as described above with respect to FIG. 2A. Application of anti-reflective coatings 212, 214 may be achieved by thin film coating technology, such as on a plurality of connectorized ferrule-fiber ends in a batch operation. As a result of anti-reflective coatings 212, 214, an improvement in optical power transmission of up to about 10% may be observed when anti-reflective coatings 212, 214 are used in fiber joint 106-2. In some embodiments, an improvement in optical power transmission of up to 8% may be observed when anti-reflective coatings 212, 214 are used in fiber joint 106-2. In some embodiments, an improvement in optical power transmission of up to 5% may be observed when anti-reflective coatings 212, 214 are used in fiber joint 106-2. It is noted that any suitable anti-reflective coating may be used.

Figure 3:
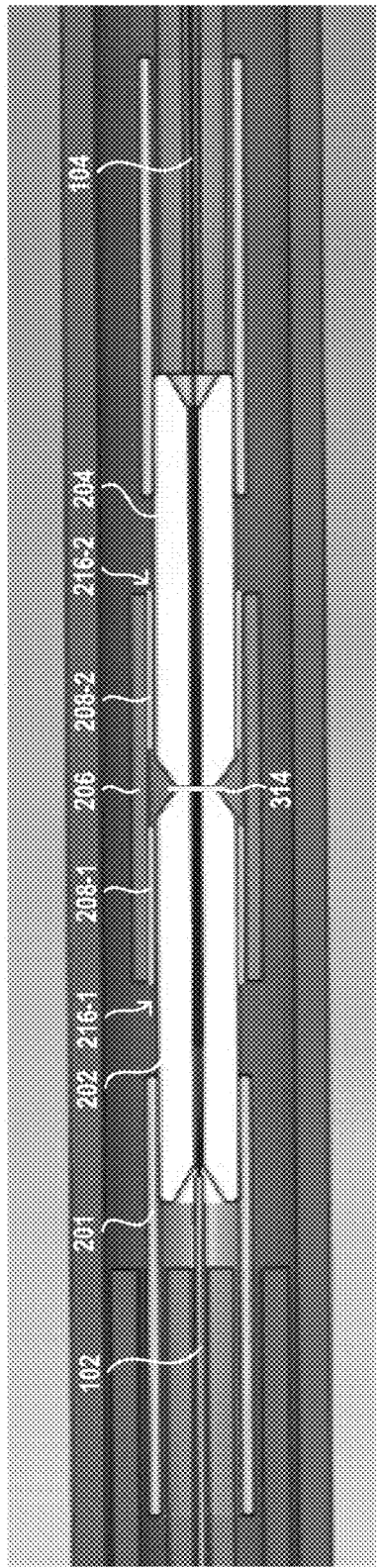
FIG. 3 is a diagram of selected embodiments of an optical fiber joint having improved reliability.

Referring now to FIG. 3, selected elements of an embodiment of an optical fiber joint 106-3 (or simply 'fiber joint') are shown. FIG. 3 is a schematic diagram and is not drawn to scale. In FIG. 3, fiber joint 106-3 is shown in a cross-sectional view, in which the depicted elements may be assumed to be radially symmetrical about a center line extending parallel to the optical fibers. FIG. 3 depicts selected elements of an embodiment of an optical fiber joint 106-3 that includes all the elements described above for fiber joint 106-1 in FIG. 2A. However, in fiber joint 106-3, an uncured optical adhesive 314 has additionally been introduced between first ferrule 202 and second ferrule 204 (corresponding to interface 210 in FIG. 2A). For example, uncured optical adhesive 314 may be applied before glass sleeve 206 is placed over first ferrule 202 and second ferrule 204. Uncured optical adhesive 314 may be applied by simply dabbing a drop of adhesive 314 between first ferrule 202 and second ferrule 204. After curing of UV-cured optical adhesive 208, uncured optical adhesive 314 may remain in the liquid phase within fiber joint 106-3 and may improve transmission between proximal fiber 102 and distal fiber 104, in various embodiments. It is noted that any suitable uncured optical adhesive may be used.

In some embodiments, a refractive index matching gel (not shown) may be applied in a similar manner as uncured optical adhesive 314 to minimize light refraction by matching the refractive index of the fiber materials to improve light transmission at fiber joint 106-3.

Figure 4:
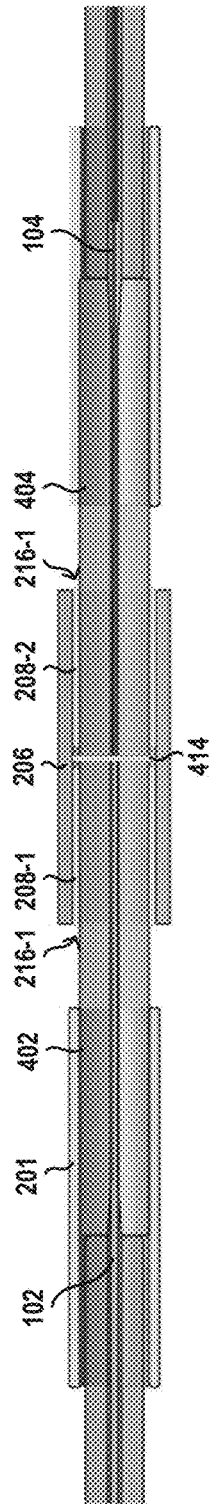
FIG. 4 is a diagram of selected embodiments of an optical fiber joint having improved reliability.

Referring now to FIG. 4, selected elements of an embodiment of an optical fiber joint 106-4 (or simply 'fiber joint') are shown. FIG. 4 is a schematic diagram and is not drawn to scale. In FIG. 4, fiber joint 106-4 is shown in a cross-sectional view, in which the depicted elements may be assumed to be radially symmetrical about a center line extending parallel to the optical fibers. FIG. 4 depicts selected elements of an embodiment of an optical fiber joint 106-4 that includes all the elements described above for fiber joint 106-1 in FIG. 2A, except that instead of ceramic ferrules 202, 204, first glass ferrule 402 and second glass ferrule 404 are used in fiber joint 106-4. Additionally, in fiber joint 106-4, third UV-cured optical adhesive 414 has been introduced between first glass ferrule 402 and second glass ferrule 404 (corresponding to interface 210 in FIG. 2A). It is noted that third UV-cured optical adhesive 414 may be comprised of the same adhesive as UV-cured optical adhesive 208.

In some embodiments of forming optical fiber joint 106-4, first and second UV-cured optical adhesive 208-1, 208-2 may be applied as described above with respect to fiber joint 106-1 in FIG. 2A, while third UV-cured optical adhesive 414 may be applied in a similar manner to uncured optical adhesive 314 described with respect to fiber joint 106-3 in FIG. 3.

In other embodiments of forming optical fiber joint 106-4, the UV-cured optical adhesive may be applied in a conventional manner, such as prior to sliding glass sleeve 206 over first glass ferrule 402 and second glass ferrule 404.

In fiber joint 106-4, third UV-cured optical adhesive 414 may be sufficiently cured along with first and second UV-cured optical adhesive 208-1, 208-2, because the use of glass ferrules 402, 404 may eliminate UV shadows from occurring that would otherwise prevent curing of UV-cured optical adhesive 414. Thus, UV-cured optical adhesive 208, 414 may fully cure and the reliability issues described above with insufficient curing and premature failure may be avoided in fiber joint 106-4, which is desirable.

Figure 5:
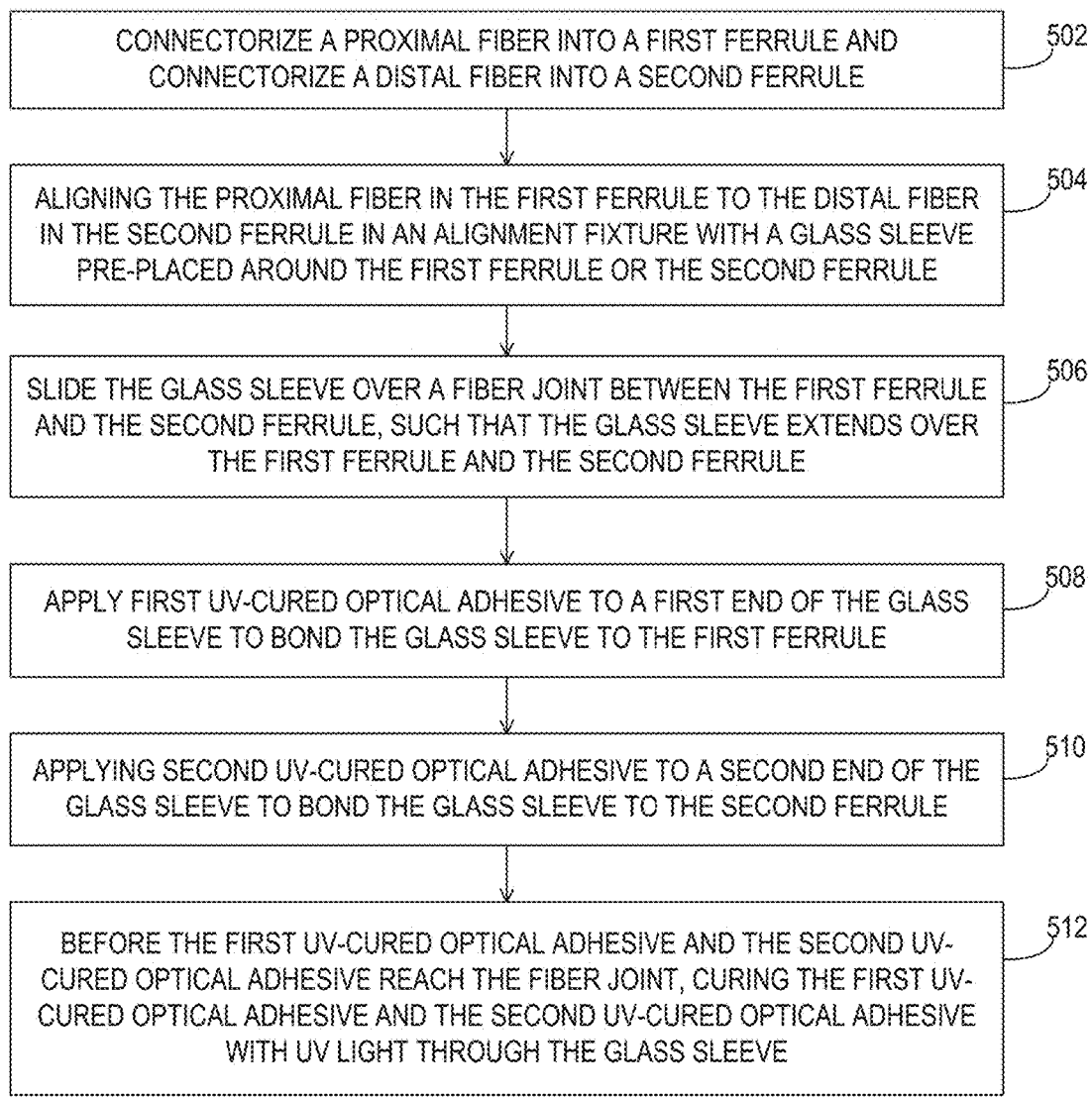
FIG. 5 is a flow chart of selected embodiments of a method for improved fiber coupling reliability.

Referring now to FIG. 5, a flow chart of selected elements of an embodiment of a method 500 for improved optical fiber coupling reliability, as described herein, is depicted in flowchart form. It is noted that certain operations described in method 500 may be optional or may be rearranged in different embodiments.

Method 500 may begin at step 502 by connectorizing a proximal fiber into a first ferrule and connectorizing a distal fiber into a second ferrule. At step 504, the proximal fiber in the first ferrule is aligned to the distal fiber in the second ferrule in an alignment fixture with a glass sleeve pre-placed around the first ferrule or the second ferrule. At step 506, the glass sleeve is slid over a fiber joint between the first ferrule and the second ferrule, such that the glass sleeve extends over the first ferrule and the second ferrule. At step 508, first UV-cured optical adhesive is applied to a first end of the glass sleeve to bond the glass sleeve to the first ferrule. At step 510, second UV-cured optical adhesive is applied to a second end of the glass sleeve to bond the glass sleeve to the second ferrule. Before the first UV-cured optical adhesive and the second UV-cured optical adhesive reach the fiber joint, at step 512, the first UV-cured optical adhesive and the second UV-cured optical adhesive are cured with UV light through the glass sleeve.

In method 500, when the first ferrule and the second ferrule are both ceramic ferrules, the UV-cured optical adhesive is not present in the fiber joint between the proximal fiber and the distal fiber. In some embodiments of method 500, prior to the aligning in step 504, an anti-reflective coating may be applied to the first ferrule at the proximal fiber and to the second ferrule at the distal fiber, such that the anti-reflective coating reduces reflection of light between the proximal fiber and the distal fiber. In some embodiments of method 500, prior to sliding the glass sleeve over the fiber joint in step 506, an uncured optical adhesive may be applied between the first ferrule and the second ferrule, such that the uncured optical adhesive remains in the liquid phase in the fiber joint. In some embodiments of method 500, prior to sliding the glass sleeve over the fiber joint in step 506, a refractive index matching gel may be applied between the first ferrule and the second ferrule.

It is noted that in method 500, the proximal fiber and the distal fiber may be made of dissimilar materials, such as silica and borosilica, among other examples. It is noted that in method 500, at least one of the proximal fiber and the distal fiber may have a diameter of less than 50 micrometers.

In method 500, when the first ferrule and the second ferrule are both glass ferrules, prior to sliding the glass sleeve over the fiber joint at step 506, a third UV-cured optical adhesive may be applied in the fiber joint between the first ferrule and the second ferrule.

As disclosed herein, improved optical fiber coupling reliability is realized by improving structures and materials used at the fiber joint. When ceramic ferrules are used at the fiber joint, the penetration of a UV-cured optical adhesive between the ceramic ferrules and the fiber ends is avoided or prevented, while an anti-reflective coating, an uncured optical adhesive, or a refractive index matching gel may be applied between the ceramic ferrules. When glass ferrules are used at the fiber joint, the UV-cured optical adhesive may be applied and fully cured between the glass ferrules and the fiber ends.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An optical fiber assembly comprising:
    a proximal fiber coupled to a distal fiber at a fiber joint, the fiber joint further comprising:
        a first ferrule connectorizing the proximal fiber;
        a second ferrule connectorizing the distal fiber and opposing the first ferrule at an interface between the first ferrule and the second ferrule, wherein at least one of the proximal fiber and the distal fiber have a diameter less than 50 micrometers;
        a single piece glass sleeve surrounding the first ferrule and the second ferrule to enable optical joining of the proximal fiber and the distal fiber at the interface with nothing between the proximal fiber and distal fiber, and wherein a diameter of the proximal and distal fibers remains substantially uniform through the glass sleeve;
        the glass sleeve bonded at one end of the glass sleeve using a first UV-cured optical adhesive to a first outer surface of the first ferrule;
        the glass sleeve bonded at another end of the glass sleeve using the first UV-cured optical adhesive or a second UV-cured optical adhesive to a second outer surface of the second ferrule;
        wherein the fiber joint further comprises an anti-reflective coating applied to the first ferrule at the proximal fiber and applied to the second ferrule at the distal fiber, wherein the anti-reflective coating reduces reflection of light between the proximal fiber and the distal fiber; and
        wherein the fiber joint transmits coherent light from a white laser source.

2. The optical fiber assembly of claim 1, wherein:
    the first ferrule and the second ferrule are both ceramic ferrules.

3. The optical fiber assembly of claim 1, wherein the proximal fiber and the distal fiber are made of dissimilar materials.

4. The optical fiber assembly of claim 1, wherein:
    the first ferrule and the second ferrule are both glass ferrules.

5. A method for coupling optical fibers, the method comprising:
    connectorizing a proximal fiber into a first ferrule;
    connectorizing a distal fiber into a second ferrule at an interface between the first ferrule and the second ferrule, wherein at least one of the proximal fiber and the distal fiber have a diameter less than 50 micrometers;
    applying an anti-reflective coating to the first ferrule at the proximal fiber and to the second ferrule at the distal fiber, wherein the anti-reflective coating reduces reflection of light between the proximal fiber and the distal fiber;
    aligning the proximal fiber in the first ferrule and the distal fiber in the second ferrule in an alignment fixture, wherein a single piece glass sleeve is pre-placed around one of the first ferrule or the second ferrule;
    sliding the single piece glass sleeve over a fiber joint between the first ferrule and the second ferrule, wherein the glass sleeve extends over the first ferrule and the second ferrule, and wherein the fiber joint has nothing between the first ferrule and the second ferrule;
    applying a first UV-cured optical adhesive to a first end of the glass sleeve to bond the glass sleeve to the first ferrule;
    applying a second UV-cured optical adhesive to a second end of the glass sleeve to bond the glass sleeve to the second ferrule; and
    before the first UV-cured optical adhesive and the second UV-cured optical adhesive reach the fiber joint, the first UV-cured optical adhesive and the second UV-cured optical adhesive are cured with UV light through the glass sleeve;
    transmitting a coherent light from a white laser source through the fiber joint.

6. The method of claim 5, wherein:
    the first ferrule and the second ferrule are both ceramic ferrules.

7. The method of claim 5, wherein the proximal fiber and the distal fiber are made of dissimilar materials.

8. The method of claim 5, wherein the first ferrule and the second ferrule are both glass ferrules.

* * * * *